United States Patent
Espada Tejedor (10) Patent No.: US 7,677,102 B2
(45) Date of Patent: Mar. 16, 2010

(54) HEAD WITH ROLLER FOR PULSE-ECHO ULTRASONIC INSPECTION OF PARTS IN AN AUTOMATIC PARTS INSPECTION FACILITY

(75) Inventor: Alvaro Espada Tejedor, Madrid (ES)

(73) Assignee: Airbus Operations, S.L., Getafe (Madrid) (ES)

( * ) Notice: Subject to any disclaimer, the term of this patent is extended or adjusted under 35 U.S.C. 154(b) by 401 days.

(21) Appl. No.: 11/716,602

(22) Filed: Mar. 12, 2007

(65) Prior Publication Data

US 2008/0066553 A1    Mar. 20, 2008

(30) Foreign Application Priority Data

Sep. 20, 2006    (ES)    ................................ 200602382

(51) Int. Cl.
*G01N 29/04* (2006.01)
(52) U.S. Cl. .............................. 73/618; 73/635; 73/641; 73/644
(58) Field of Classification Search ................... 73/618, 73/635, 640, 641, 644
See application file for complete search history.

(56) References Cited

U.S. PATENT DOCUMENTS

| | | | |
|---|---|---|---|
| 3,752,255 A * | 8/1973 | Hill et al. ...................... 73/596 |
| 4,162,636 A * | 7/1979 | Lather et al. ................... 73/638 |
| 4,277,979 A * | 7/1981 | Vilkomerson et al. ......... 73/633 |
| 4,469,106 A * | 9/1984 | Harui ........................... 600/461 |
| 5,005,417 A * | 4/1991 | Kawasaki et al. ............. 73/593 |
| 5,535,628 A * | 7/1996 | Rutherford .................... 73/622 |
| 5,690,110 A * | 11/1997 | Tanaka ........................ 600/446 |
| 5,814,731 A * | 9/1998 | Alexander et al. ............ 73/644 |
| 2007/0074573 A1* | 4/2007 | Ester et al. ..................... 73/660 |
| 2009/0010285 A1* | 1/2009 | Dubois et al. .................. 372/3 |

* cited by examiner

*Primary Examiner*—Hezron Williams
*Assistant Examiner*—J M Saint Surin
(74) *Attorney, Agent, or Firm*—Wenderoth, Lind & Ponack, LLP.

(57) ABSTRACT

A head for ultrasonic inspection with a semidry coupling system involving a roller (4) and an ultrasound scanner that rolls on the surface (5) of the part to be inspected, includes a first frame (1) to which the roller (4) is connected and pivots around a stationary axis (4a) in a direction that is perpendicular to the probe's movement; a second frame (2) from which linear vertical guides (6) emerge and is connected in an oscillatory manner to the first frame (1) through an oscillating axis (11a) that is perpendicular to the stationary axis (4a): a third frame (3) that slides vertically through the linear guides (6); and at least two actuators of vertical adjustment (9) anchored to the third frame (3) and to the second frame (2), their corresponding laterally aligned pivotal axes (10), connected to the first frame (1) in a rotating manner and parallel to and lower from the plane of the stationary axis (4a) and the respective ends of the stationary axis (4a).

17 Claims, 8 Drawing Sheets

HEAD WITH ROLLER FOR PULSE-ECHO ULTRASONIC INSPECTION OF PARTS IN AN AUTOMATIC PARTS INSPECTION FACILITY

TECHNICAL FIELD OF THE INVENTION

The present invention falls within the technical field of non-destructive inspection of parts of composite materials by means of ultrasound techniques, and more particularly, the present invention refers to a head with a roller for the ultrasonic inspection by pulse echo, that can be coupled to automatic inspection installations of parts manufactured from composite materials of large dimensions, particularly of parts used in the aeronautic industry.

STATE OF THE PRIOR ART

Ultrasonic inspection is today a process habitually used for the non-destructive inspections of parts made of carbon fiber. More particularly, the ultrasonic inspection technique by pulse echo is based on introducing elastic mechanical waves in the material to be inspected that then propagate and experience reflection, refraction, attenuation, diffraction, etc. The waves do not experience any of these phenomena in the presence of homogenous materials, while if the material shows any defect the waves are not continuous. A coupling means, such as water, is necessary for the adequate transmission of ultrasound waves. Conventional pulse echo ultrasonic inspection processes are based, essentially, in automatic machines with multiple channels for the inspection of large flat surfaces and in manual mono-channel and multi-channel systems for the inspection of small surfaces.

The automatic systems used to date for ultrasonic inspection use rigid or semi-rigid heads made by one or more scanners with coupling achieved by local immersion in the part to be inspected, being then appropriate for flat or semi flat parts, but having difficulty inspecting curved parts, since the rigid head could not adapt adequately to the variations of the surface to be inspected, and therefore, the rigid head could not keep contact with the surface, preventing ultrasonic coupling and hence the correct and complete analysis of the part.

On the other hand, there are also known semidry coupling systems that are coupled to the part to be inspected. These systems are composed of an ultrasonic scanner housed inside a roller (or rolling device) made of or clad in a special hydrophilic rubber with ultrasonic properties similar to those of water that optimize ultrasonic coupling between the part and the scanner, and therefore allow maximizing the scanner's incoming and outgoing energy. NDT Solutions has developed this type of ultrasonic roller scanner sensor. However, in this type of semidry coupling system there is still the problem of there not being head scanners that can be coupled efficaciously to facilities intended for the complete and automatic piezo inspection of parts with larges surface, such as aeronautic parts of large aerodynamic surfaces like wings, stabilizers and fuselage sections of a plane.

SUMMARY OF THE INVENTION

The object of the present invention is to overcome the current disadvantages of the art as specified above, by means of a head that includes, at least, a conventional or multielement (phased array) ultrasound scanner housed inside a roller capable of rolling over the surface of the part to effect the pulse echo ultrasonic inspection of carbon fiber parts, and that has a first frame in which the roller pivots around a stationary axis arranged perpendicularly to the direction in which the head moves, a second frame from which vertical linear guides emerge and that is connected to the first frame in a swiveling arrangement, a third frame, that slides vertically by means of the linear guides, and coupling means to couple the third frame to an automatic motion installation which probe has also the following characteristics.

Each of the ends of the roller's stationary axis are connected to vertical connection means that are connected to the first frame by aligned lateral pivoting axis that allow a swiveling motion and are located in a lower plane than the stationary axis displacing the pivoting axis downwards, which position allows positioning the ultrasound scanner or scanners housed inside the roller perpendicular to the surface on which the roller rests. This perpendicular position is the optimum position for ultrasonic inspection. The means of vertical connection may be vertical clamps that have, each one, an upper part connected to an end of the respective stationary axis and a lower part connected to one of the pivoting axles, in such a manner that each pivoting axle is connected between a vertical clamp and the adjacent part that is the first frame. Also, the vertical means of connections may be equipped with shock absorbers to minimize the effect of the mechanical tilts on the roller. These tilts are caused, for instance, during the acceleration and deceleration phases during scan sweeps, and may cause small changes in the perpendicularity of the scanner or scanners in relation to the surface over which the roller is rolling. The shock absorbers minimize, and even cancel, these tilts, and therefore, the information registered by the scanner or scanners is not affected by said tilts. The shock absorbers may be, for instance, ball bearings SNL series manufactured by the SKF Company in Sweden.

The first frame is connected to the second frame by articulating means in such a manner that these frames can oscillate about at least one pivoting axle that is perpendicular to the stationary axle, so that the roller is kept in contact with the surface of the part being inspected, even when the part presents a lateral tilt. In a preferred embodiment of the invention, the first frame is a quadrangular frame that includes two first opposite sides from which the corresponding vertical plates emerge in a downward directions and to which each of them one of the pivoting axles is connected and two second opposite sides on which the corresponding first articulation means, that are complementary to the second articulation means of the second frame, are affixed. The first articulation means may include the corresponding articulation axles arranged in opposite sides from the first frame, in which case the second articulation means may include complementary housings located in the corresponding plates that emerge from below in the opposing sides of the second frame. Alternatively, the first articulation means may include housings in corresponding plates that emerge from above the first frame, in which case, the second means of articulation may include the corresponding articulation axis arranged in the opposite sides of the second frame.

The second frame is connected to the third frame by at least two actuators for vertical adjustment, that may be pneumatic, hydraulic or electromechanic, and that are, each one of them, connected by their outer upper part to an end part of the third frame, and connected by their lower end part to an end part of the second frame. Each pneumatic actuator may entail an actuator body anchored to the third frame and an actuating shank coupled by its free end to the second frame. In this manner, through the operation of the actuating shank, the second frame can be brought closer to or further from the third frame, and therefore the roller coupled to the first frame can be pressed against, or removed from the part on which is rolling. Additionally, when the roller equipped with ultrasonic scanner or scanners has a cladding of elastically deformable hydrophilous rubber, the pressure exerted by the pneumatic actuators serves to press the rubber cladding against the surface on which the roller is rolling, achieving, through the subsequent deformation of the rubber, an optimized coupling to the surface. Preferably, each pneumatic actuator is arranged in an intermediate position between a pair of linear guides. Also, and to allow the third plate to slide very smoothly on the linear guides when the pneumatic actuators are operated, the third plate may be equipped with linear ball bearings through which the linear guides extend. To control the pressure of the pneumatic actuators, the head may be equipped with a pressure regulator controlled by a control circuit governed by a software program. This regulator controls the pressure of the pneumatic actuators and is fed by a conventional network of compressed air. Also, the head may be equipped with a barometer to indicate the pressure at the cylinders, which pressure can be modified by means of the pressure control knob of the pneumatic system.

The articulation of the roller to the first frame by means of the "displace pivoting axle", aided by the pressure exerted by the pneumatic actuators, causes the ultrasonic scanner or scanners housed inside the roller to achieve a perpendicular position from the surface inspected (as well as the optimum deformation of the rubber cladding of the roller, if any), that achieves the coupling necessary to gather the ultrasonic data. In this manner the displaced pivoting axle reduces the requirements of the automatic installation in what regards the creation and execution of traveling paths, precisely because the ultrasonic scanner or scanners, and hence the ultrasound beams, have successfully achieved perpendicularity from the surface being inspected. Also, and according to the statements above, the plate that joins the displaced axle to the first frame contains additional means to guarantee perpendicularity, based on the mechanism of self-aligning ball bearings that provide the necessary freedom for the roller to roll smoothly over the surface to be inspected. On the other hand, the set of guides—holding plates, provides the assembly the necessary rigidity for the second frame, and therefore for the roller bearing first frame as well, to travel smoothly up and down, which is a necessary requirement for the characteristics of the ultrasonic coupling not to vary during the inspection. On the other hand, the fact that the second frame oscillates on the first frame through a coaxial pivot axle in the direction of travel of the roller, provides the necessary degree of freedom for the roller to inspect the different geometric configurations of the surfaces to be inspected.

In a preferred embodiment of the invention, the head also includes, at least, a maximum tilt sensor placed in the first frame and connected to an electronic control system. Preferably there will be two of such sensors, one placed at the front and another at the back of the roller. The maximum tilt sensors are used to detect an excessive tilt of the surface inspected, that would translate into a limitation of the quality of the information obtained. In this manner, if the roller is positioned on a part, or on an area in which the scanner or scanners cannot be perpendicularly placed relative to the surface to be inspected, the maximum tilt sensors detect this event and emit the appropriate signal, that is transmitted to the control unit, itself connected to a software tool that in this case would not allow the inspection to start. Another function of the maximum tilt sensors is to avoid possible damage to the part and/or to the roller when, due to the geometric characteristics of the surface to be inspected, the roller reaches maximum tilt values, in which case the maximum tilt sensors emit the appropriate signal that is then processed by the program at the control unit that in turn commands an emergency stop and causes the actuators to lift the second frame, and therefore the roller. The maximum tilt sensors also act when the roller travels over parts that have steps or windows and to detect that the end of the part has been reached. In these cases the maximum tilt sensors also emit the appropriate signal, the signal is also processed by the program at the control unit that issues an emergency stop command and causes the actuators to lift the second frame, lifting the roller from the surface of the part being inspected.

In another embodiment of the invention, the head also includes, at least, a system to block tilting movements that prevents and/or at least avoids the tilt between the first and the second frame. This system is useful when the flexibility of movements provided by the tilt of the first frame in respect to the second frame. This system is useful when the flexibility of movement provided by the tilt of the first frame over the second frame allows the expected results to be obtained during the inspection of the part, when the roller is going over areas of the part on which does not have a full purchase, such as may be the case during inspection of edges of parts, edges of windows, stages, etc. The system then acts by blocking or, depending on the need at hand, merely limiting, the tilt of the first frame over the second frame, so they only movement, or basically the only movement enabled is the turn of the roller and the movement according to the displaced axle.

The blocking system of the tilting movements between the first and the second frames may entail, at least, a blocking plate that emerges laterally from the second frame and that is arranged is such a manner that it abuts or leans against the first frame when tilting between the first and second frame reaches a preset maximum tilting angle. Alternatively, or complementarily, the blocking system may comprise, at least, a support for auxiliary elements that limits the tilt and emerges from one of the second sides of the first frame pointing towards one of the first sides of the frame, in such a manner that it abuts or comes in contact with the second frame when tilting between the first and the second frame reaches a maximum preset angle of tilt.

Also alternatively or complementarily, the blocking system may comprise at least an adjustable tilt blocking system that itself comprises an actuator selected from pneumatic actuators, electromechanic actuators and hydraulic actuators connected by its lower end to one of the first sides of the first frame and by its upper end to the second frame. The actuator allows the free tilting of the first frame in relation to the second frame, provided it is not activated. Operating the actuator, regardless of the position the first frame in relation to the second frame at the time, prevents the tilting movement and guarantees that the relative position between the first and second frames is kept constant. Once the actuator is stopped, the free tilting movement between first and second frame is regained. The company Provindus is an example of a provider that manufactures adequate blocking actuators to use in conjunction with the head object of the present invention.

The second frame may also comprise, at least, a maximum tilt sensor placed on the second frame and connected to an electronic control system that reacts during conditions similar to those described as applicable for the maximum tilt sensor installed on the first frame.

Conveniently, the head can also be equipped with diffuser water spouts that spray atomized water and are connected to a pressurized water supply system and arranged on the first frame oriented so they spray the atomized water over the roller and over the surface of the part being inspected in the direction of the roller's travel path, which is applicable also when the roller used is a manufactured roller or it has a hydrophilous rubber elastically deformable cladding or envelope, of the type described above, and used for the type of inspection requiring semidry coupling of the roller on the surface of the part inspected. The water is the ultrasonic coupler that is used in the present invention. In this case, it is also advisable to lay underneath the second frame a protective cover, for instance a plastic cover, to prevent accidental contact of the water sprayed by the diffusing nozzles with the second frame and the elements it contains, thus minimizing the possible corrosive effects that the metal elements of the invention may incur. Preferably, the nozzles are of the rapid connection type, so they can be easily changed. Depending on the type of verification inspection that needs to be done, nozzles with different types of spouts can be used to spray the amount of water necessary for a good ultrasonic coupling, and that are equipped with fast connecting means to a low pressure water circuit, with for example, 5 mm section transparent plastic tubing. The water pump is controlled from the control system. The circuit may also be equipped with at least one filter, and preferably comprises a circuit that allows the water that comes out of the nozzles to be reused by means of a collection circuit that is in turn connected to the pump.

To couple the head, that is the object of the present invention, to an automatic ultrasonic inspection installation, the third frame may be equipped with direct means of anchorage, or it can be connected with an intermediate anchoring device that is affixed both to the third frame and to the installation.

BRIEF DESCRIPTION OF THE FIGURES

This section contains descriptions of aspects of the invention that use the following drawings or figures as references. These drawings are an integral part of this descriptive report in which.

The elements shown in these figures are identified by the following numerical references:

| | |
|---|---|
| A | Head |
| 1 | first frame |
| 1a, 1b | first sides of the first frame |
| 1c, 1d | vertical plates |
| 1e, 1f | second sides of the first frame |
| 2 | second frame |
| 2a | central part of the second frame |
| 2b | end parts of the second frame |
| 2c | anchoring wholes for vertical guides |
| 2d | lower anchoring sites for pneumatic actuators |
| 3 | third frame |
| 3a | central part of the third frame |
| 3b | end parts of the third frame |
| 4 | roller |
| 4a | stationary axle |
| 4b | elastic and hydrophilic cladding material |
| 5 | surface of a part to be inspected |
| 6 | linear vertical guides |
| 7 | coupling means |
| 8 | automatic inspection installation |
| 9 | pneumatic actuator |
| 9a | actuator's body |
| 9b | actuator shank |
| 10 | lateral pivot axles |
| 10a | pivot axle housings |
| 10b, 10c | vertical platens |
| 11a | tilting axle |
| 11b, 11c | first articulation means |
| 11d, 11e | second articulation means |
| 12 | plates emerging upwards (from below) |
| 13 | linear ball bearings |
| 14 | adjusting means to ensure perpendicularity/ball bearings |
| 15 | maximum tilt sensor |
| 16 | atomizing water nozzles |
| 17a | maximum tilt limiting plate |
| 17b | tilt blocking system |
| 17c | support for auxiliary elements and tilt limiter |
| 18 | plastic protective cover |
| 19 | slot for scanner cables |
| 20 | water pump |
| 20a | used water inlet |
| 20b | fresh water inlet |
| 20c | water discharge outlet |
| 21 | faucet to supply water to the nozzles |
| 22 | water filter |
| 23 | distributor |
| 24 | collected water circuit |
| 25 | fresh water conduit |
| 26 | water supply conduit |

DETAILED DESCRIPTION OF THE INVENTION

Figure 1:
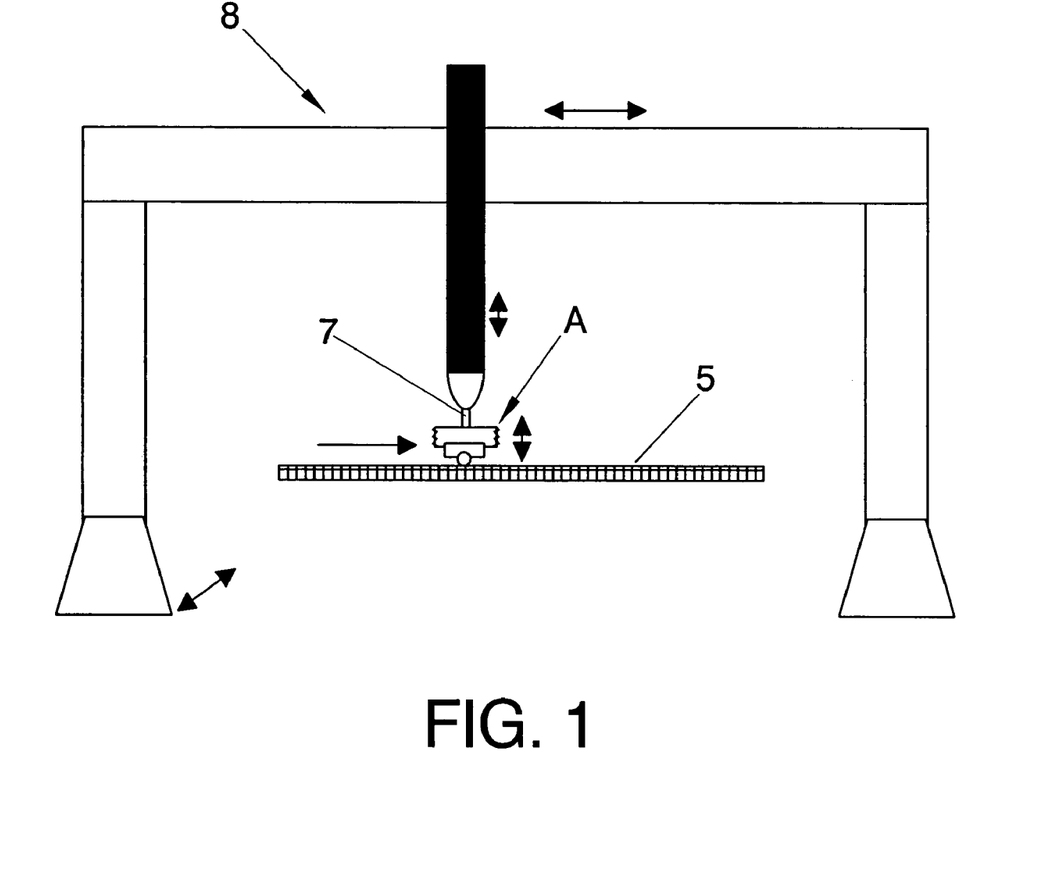
FIG. 1 is a schematic view of the lateral profile of a gantry type automatic inspection installation of parts on which a head, that is the object of the present invention, has been mounted.

FIG. 1 shows in a general overview, a mobile gantry type automatic inspection installation 8 on which a head A is mounted according to one of the embodiments of the present invention. Evidently, the installation of head 8 is not limited to this type of automatic installation, and can also be assembled in other conventional systems, such as for instance, mobile bridge systems, robotic arm systems and systems in which the part susceptible to inspection travels in relation to the head. It can be observed that in the embodiment shown in FIG. 1, head A is coupled to installation 8 by means of coupling means 7, in a manner that head A can travel over the surface 5 of a part to be inspected.

In the embodiment of head A shown in FIGS. 2 to 16, the head comprises a roller 4, susceptible to roll over surface 5 of the part to be inspected. The roller 4 comprises a cladding 4b made of hydrophilous plastic material 4b that is also elastically deformable. Inside roller 4 there is at least one ultrasound scanner (not shown in the figures) housed to effect the ultrasonic inspection by pulse echo on the parts to be inspected. The roller pivots around a stationary axle 4a placed perpendicularly to the direction of travel of head A. The unit comprised by roller/scanner (s) is in itself conventional.

Roller 4 is connected to a first frame 1 that itself is connected in a tilting manner to a second frame 2 from which vertical linear guides 6 emerge, on which a third frame 3 slides. The third frame 3 comprises the coupling means 7 to couple head A to the automatic inspection installation. The second frame 2 and the third frame 3 are mutually connected also by two pneumatic vertical adjustment actuators 9 that are themselves connected to a pneumatic compressed air supply system that is in itself conventional (not shown in the figures).

As depicted in FIGS. 2 to 6, the first frame 1 is a quadrangular frame that has two first opposing sides 1a, 1b from which the corresponding downwardly facing vertical plates 1c, 1d emerge, and two second opposite sides 1e, 1f from which the corresponding articulation axles 11b, 11c emerge. Inside the second set of sides 1e, 1f and close to the first side 1c of the first frame 1, the corresponding tilt sensors 15 have been mounted and which function has been previously described in the "Summary of the invention" section of the present descriptive report. On side 1a of the first frame 1 there is an inlet slot 19 shaped as an inverted "T" through which the connection cables (not shown in the figures) can be inserted and connected to the scanner housed inside roller 4.

Figure 2:
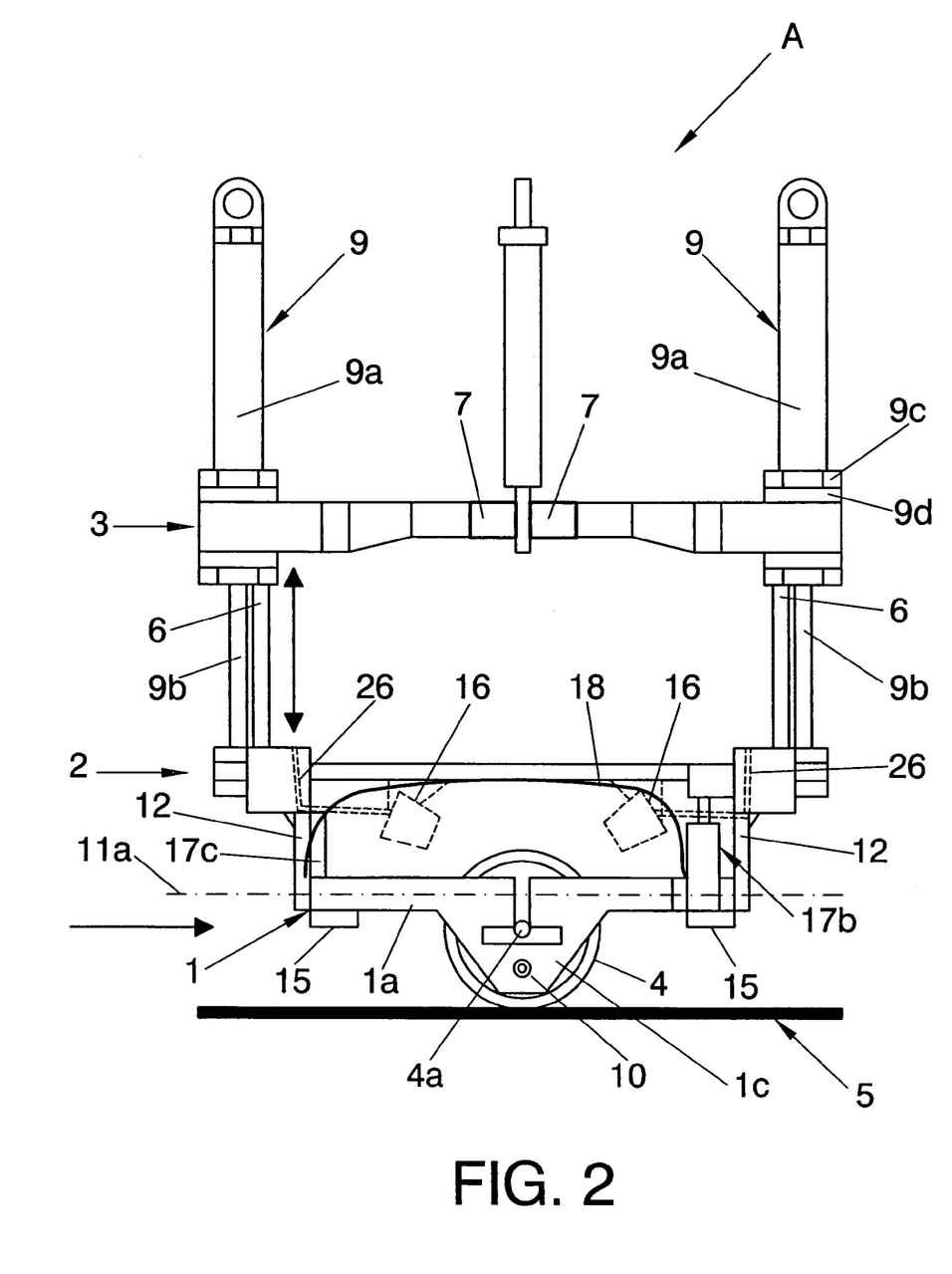
FIG. 2 is a lateral schematic view of one embodiment of the head of the present invention.
Figure 3:
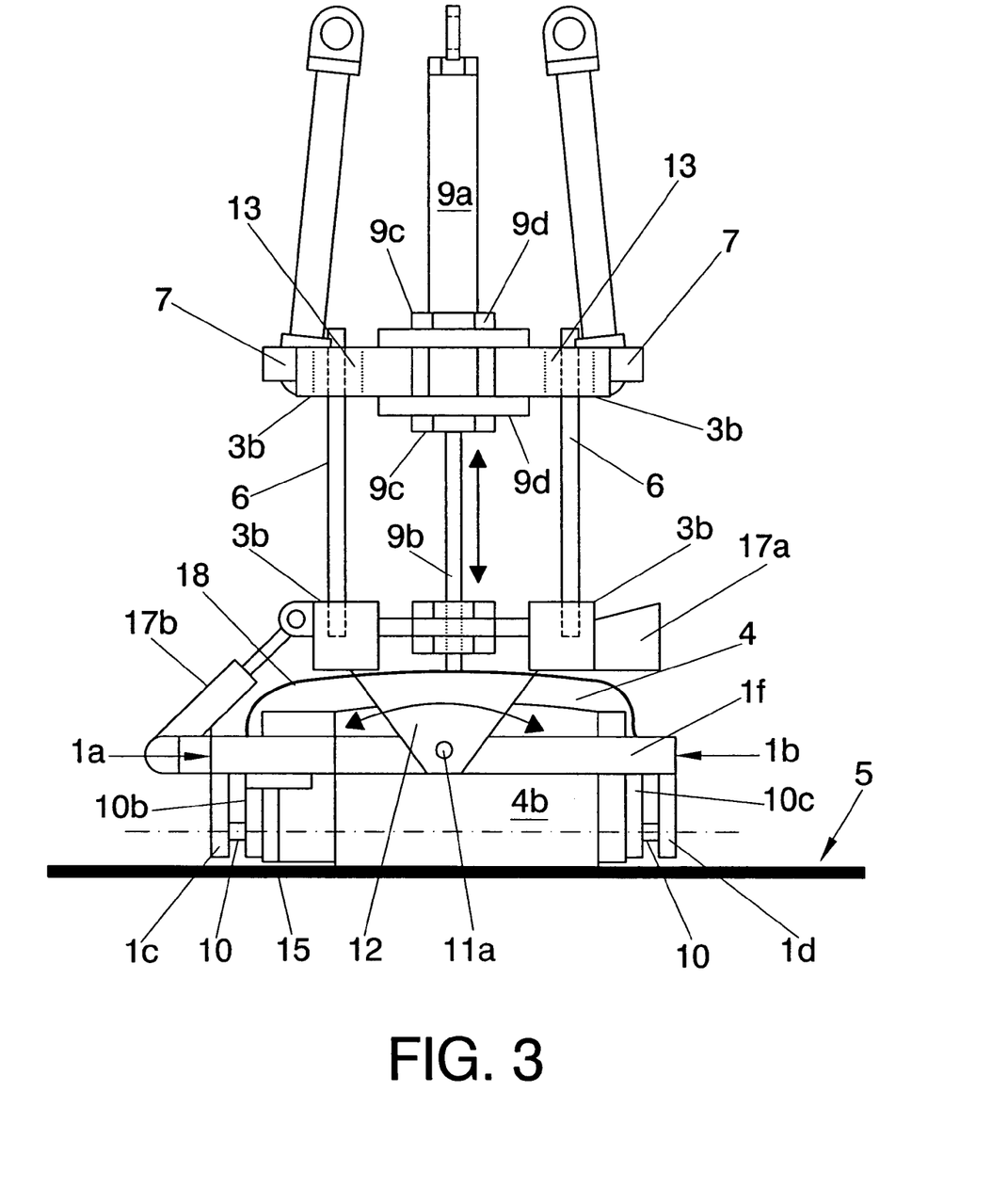
FIG. 3 is a schematic view of a frontal profile of the head depicted in FIG. 2.
Figure 4:
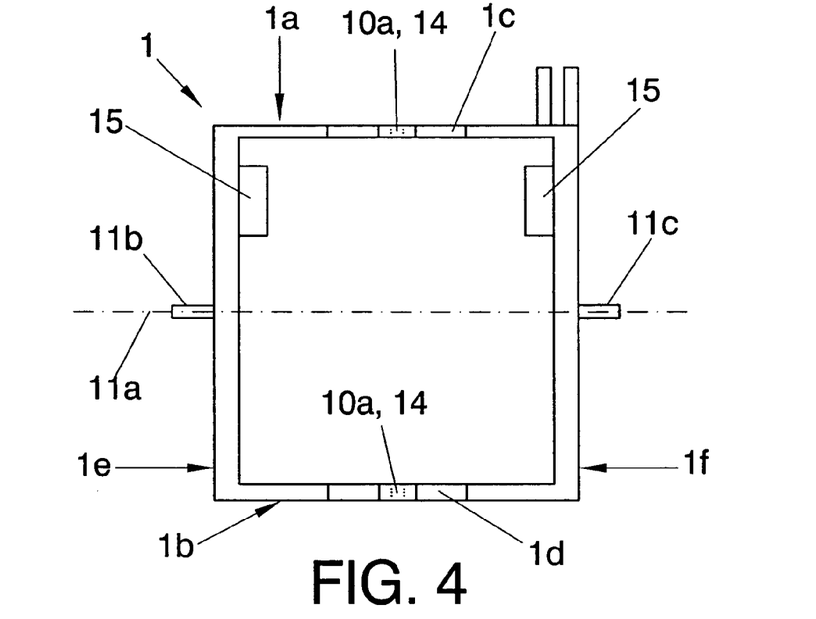
FIG. 4 is a lower schematic plant view of the first frame of the head depicted in FIG. 2.
Figure 16:
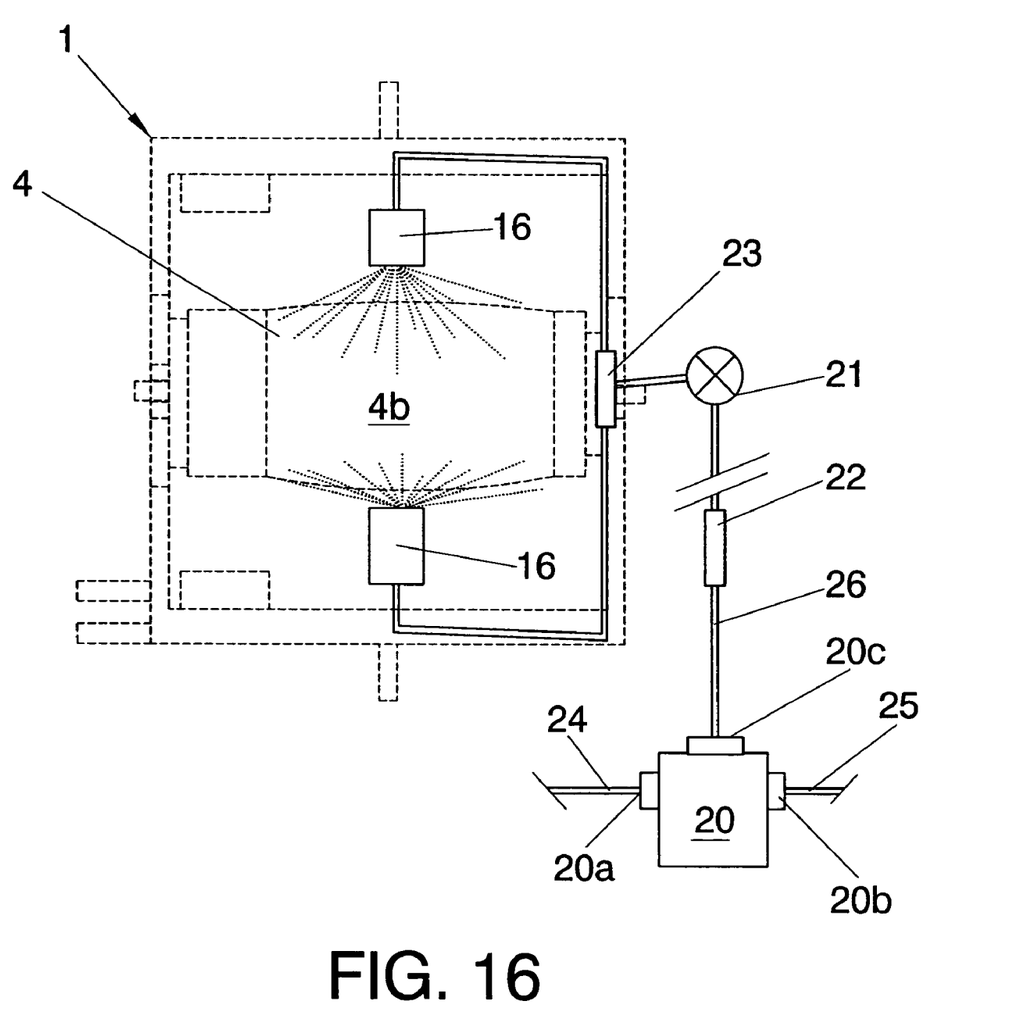
FIG. 16 is a schematic view of one embodiment of the system that supplies water to the heads according to the present invention.

FIGS. 2, 3, and 7 to 9 show appreciably the second frame 2, comprising a central part 2a and its corresponding end parts 2b. In each of the end parts 2b there are two anchoring holes 2c (shaped as blind wholes with inner thread in corresponding blocks) placed in opposite sides to anchor the two vertical linear guides 6, and between the anchoring orifices 2c and displaced outwardly, there is a lower anchoring point 2d that serves to anchor the lower part of the actuating shank 9a of the pneumatic actuator 9. A plate 12 emerges downwardly between each end part 2b and the central part 2a of second frame 2, and plate 12 has a housing 11d, 11e in its lower part that is complementary to the respective axle 11b, 11c of the first frame 1. The articulated coupling of axles 11b, 11c respectively inside housing 11d, 11e allows the first frame 1 and the second frame 2 to tilt in relation to each other on the tilt axle 11a, that is perpendicular to the stationary axle 4a of roller 4. According to what can be seen in FIGS. 3 and 7 to 9, the second frame 2 is also fitted with a blocking plate 17a, that emerges laterally from the second frame 2. Blocking plate 17a is arranged in such a manner that it abuts first frame 1, coming in contact with it when the tilt movement between first frame 1 and second frame 2 reaches its maximum tilt angle as preset. FIG. 2 also illustrates that in the lower part of second frame 2 there are two water atomizing nozzles 16 assembled, one of them being oriented to spray atomized water over roller 4 from the front side of head A, and the other being oriented to spray atomized water on roller 4 from the rear side of head A. In this manner, cladding 4a of roller 4 is impregnated with water and the surface 5 of the part susceptible to inspection is also wetted, thus creating a liquid medium that facilitates acoustic coupling between the scanner and the piece. The assembly foresees a protective plastic cover 18 (FIGS. 2 and 3) to be placed between first frame 1 and second frame 2 to avoid water from splashing. This protective cover encloses roller 4 and nozzles 16 over and laterally. FIG. 16 offers a sample view in which nozzles 16 are connected to a water supply circuit that comprises a pump 20 having a used water inlet 20a, a fresh water inlet 20b and a water discharge outlet 20 that supplies water to nozzles 16. The used water inlet 20a receives through conduct 24, water that had already been atomized through the nozzles and later collected in trays (not shown in the figures) placed underneath the piece being inspected, while the inlet 20b receives fresh water from the water network. Pump 20 expels water through discharge outlet 20c into conduit 26 that is bifurcated in two branches by a distributing element 23, each branch is then connected to one of the nozzles 16. Before reaching nozzles 16, the water goes through a filter 22 to avoid the water reaching the nozzles carries any particle that may obstruct the nozzles, or chemical or physical agents that may distort the measurements taken or negatively affect the properties of the part being inspected. Also, conduit 26 is fitted with a faucet that serves to cut the water supply going to the nozzles.

According to what can be seen in FIGS. 2, 3, and 10 to 12, the third frame 3 comprises a central part 3a, delimited between the corresponding end parts 3b. The corresponding linear bearings 13 are arranged in opposite sides of each of the end parts 3a of third frame 3, over which the corresponding linear guides 6 are laid. The end parts 3b comprise the corresponding inlets 3c, each of which immobilizes the lower part of body 9a of one of the two actuators 9, in a manner that is in itself conventional, by means of a pair of clamps 9d, upper and lower, that have a width greater than the inlet 9 and are caught between two nuts 9c that thread, respectively, onto the lower part of body 9 above and below the end part 3b of the third frame 3. Also, from each edge of the central part 3a, two flat pieces 7 held apart by an interstice 3d, emerge horizontally, their function being to couple head A to the automatic installation inspection, or to an intermediate element (not shown in the figures) onto which head A is coupled and that itself is mounted in turn on installation 8.

According to what can be seen in FIGS. 2 and 13 to 15, the ends of the stationary axle 4a of roller 4 are connected to their respective vertical connection means as vertical clamps 10b, 10c. Each vertical clamp 10b, 10c comprises an upper part connected to the end of its respective stationary axle and a lower part connected to a pivot axle 10, in such a manner that each pivot axle 10 is connected between a vertical clamp 10b, 10c and the neighboring part configured as vertical plate 1c,1d that emerges downwards from the respective side 1a, 1b of first frame 1. The pivot axles 10 are mutually aligned and pivotally connected to vertical clamps 1c, 1d of first frame 1 by the corresponding lateral pivot axles 10 aligned and placed in a plane lower than the plane of the stationary axle 4a. In this manner the pivot axles 10 form a pivot axle for roller 4 that is downwardly displaced. This configuration enables the positioning of the ultrasonic head housed inside roller 4 in a perpendicular position from the surface of the part to be inspected 5, on which roller 4 is leaning. This perpendicular position of the head is the optimum position to effect the ultrasonic inspection. Pivot axles 10 are coupled to the first frame by self-aligning ball bearings 14 that act as adjusting means and ensure that the relation of perpendicularity between roller 4 against the part's surface 5 is ensured at all times while roller 4 travels along the surface.

Figure 5:
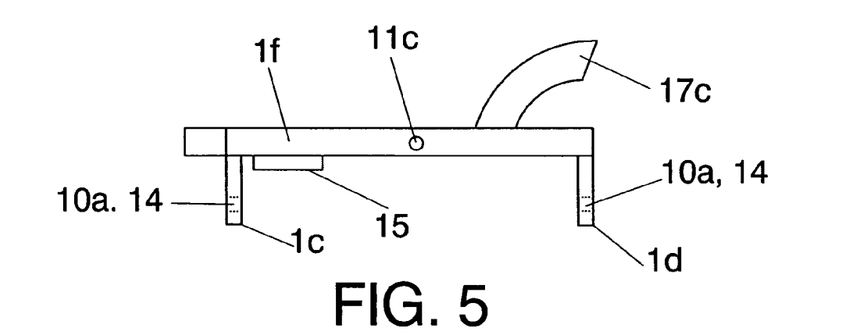
FIG. 5 is a frontal schematic view of the first frame of the head depicted in FIG. 2.
Figure 6:
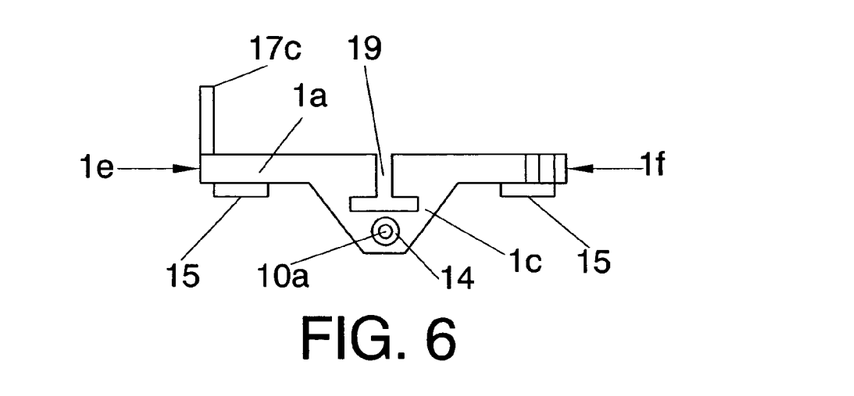
FIG. 6 is a lateral schematic view of the first frame of the head depicted in FIG. 2.
Figure 7:
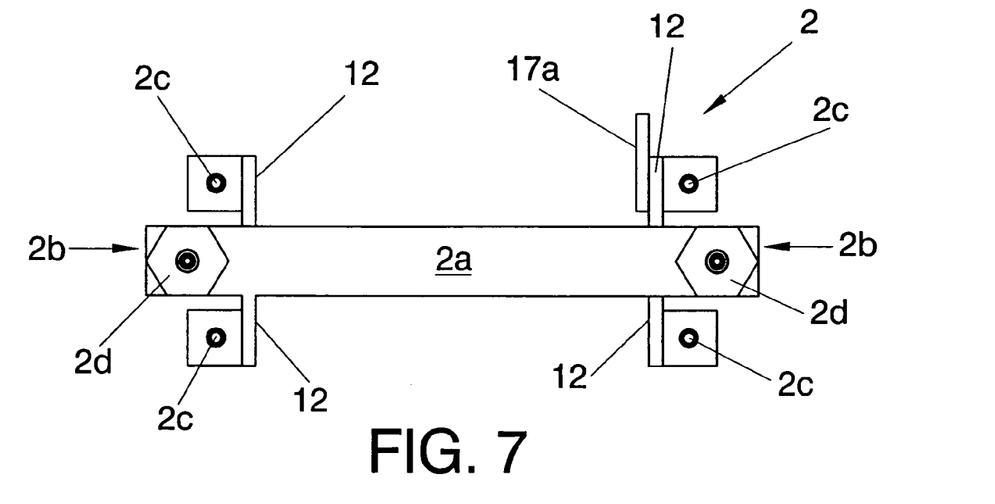
FIG. 7 is an upper plant schematic view of the second frame of the head depicted in FIG. 2.
Figure 8:
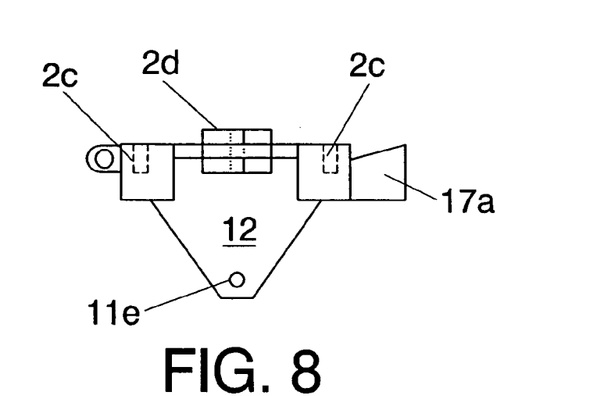
FIG. 8 is a frontal schematic view of the second frame of the head depicted in FIG. 2.
Figure 9:
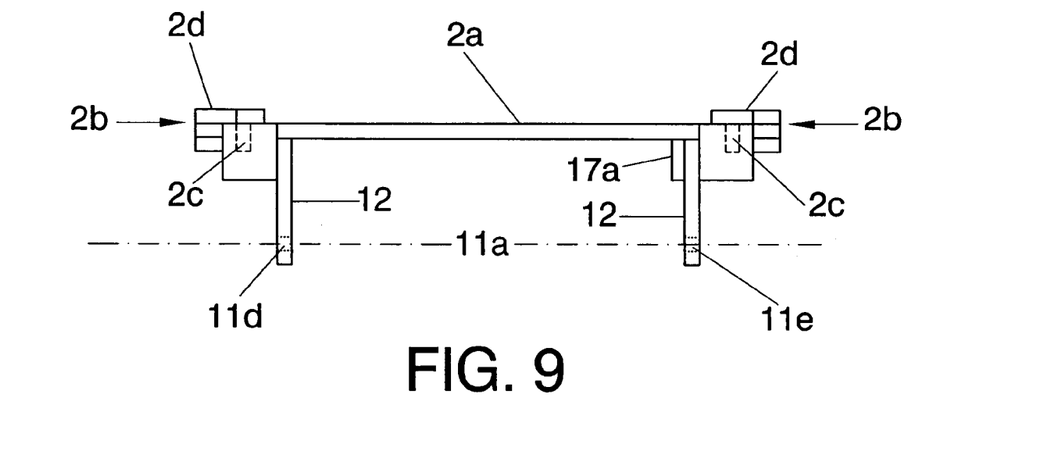
FIG. 9 is a lateral schematic view of the second frame of the head depicted in FIG. 2.
Figure 10:
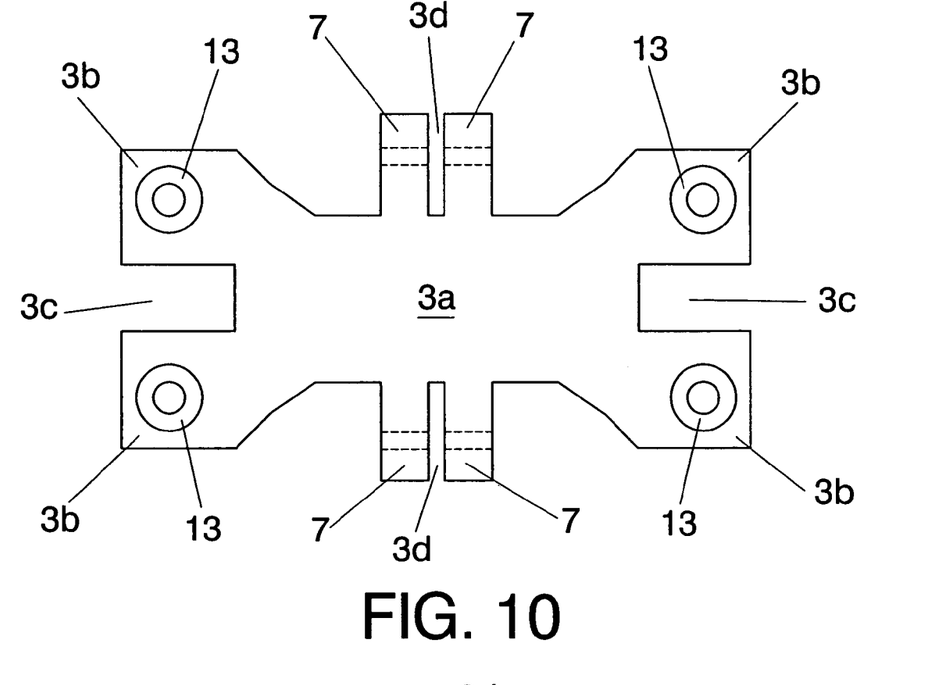
FIG. 10 is an upper plant schematic view of the third frame of the head depicted in FIG. 2.
Figure 11:
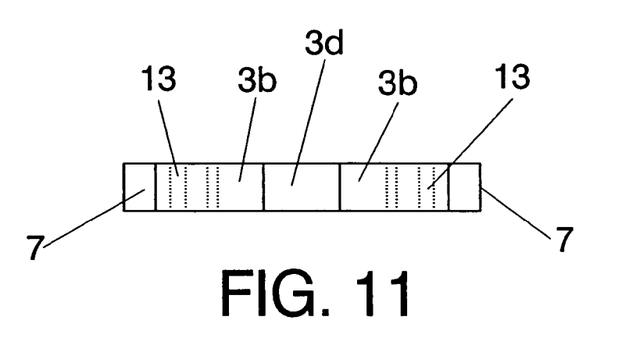
FIG. 11 is a frontal schematic view of the third frame of the head depicted in FIG. 2.
Figure 12:
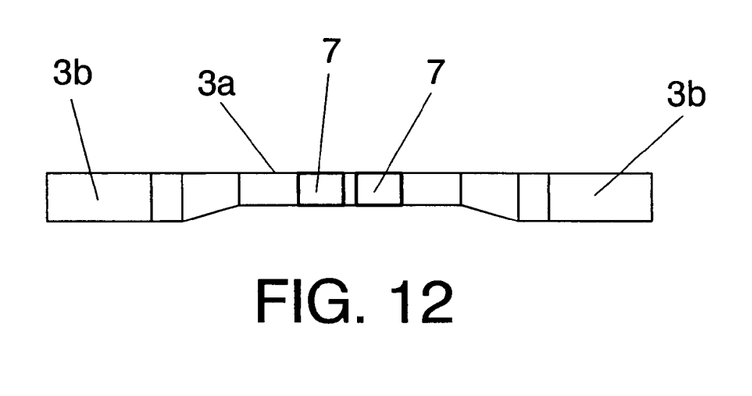
FIG. 12 is a lateral schematic view of the third frame of the head depicted in FIG. 2.
Figure 13:
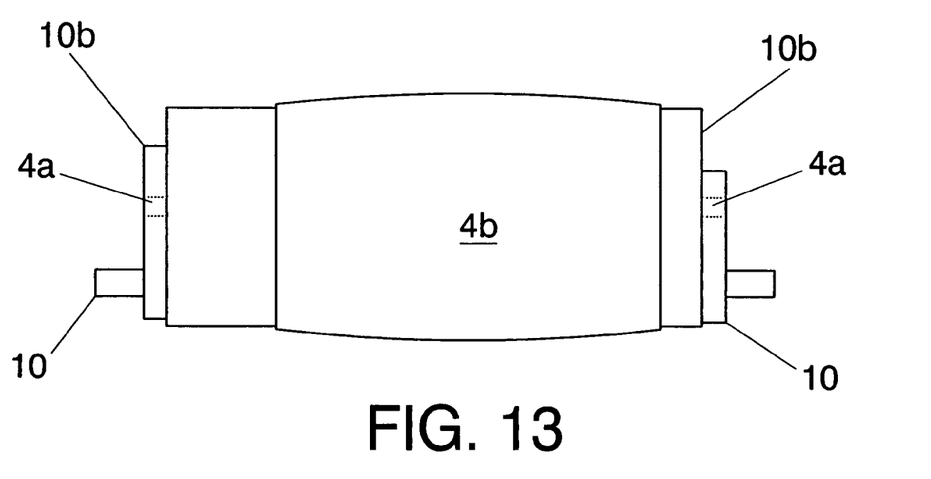
FIG. 13 is a schematic view of the frontal profile of the third frame of the roller of the head depicted in FIG. 2.
Figure 14:
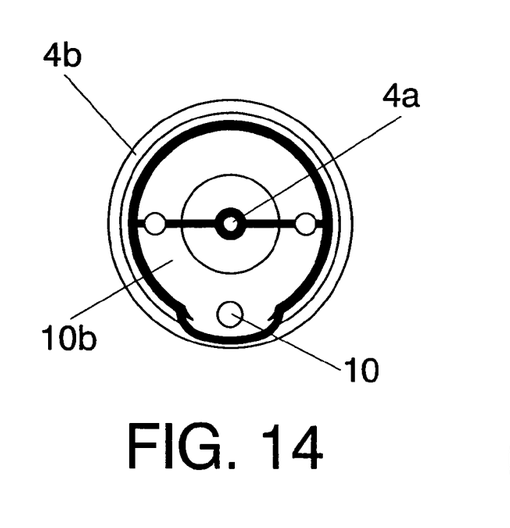
FIG. 14 is a partial lateral schematic view of the left side of the roller depicted in FIG. 13.
Figure 15:
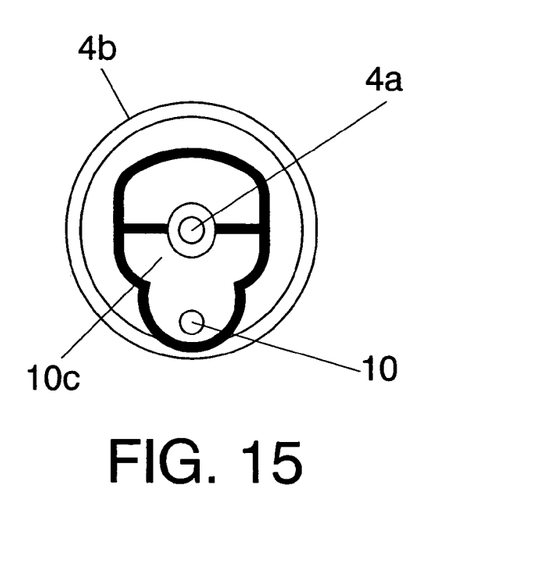
FIG. 15 is a partial lateral schematic view of the right side of the roller depicted in FIG. 13.

In the embodiment of the invention shown in FIGS. 2 to 15, head A comprises also several blocking systems of the tilting movement range that exists between first frame 1 and second frame 2. And, as shown in FIGS. 3 and 7 to 9, second frame 2 is equipped with a blocking plate 17a that emerges laterally from the second frame 2. Blocking plate 17a is arranged in such a manner that when the tilting movement between first frame 1 and second frame 2 reaches a preset maximum tilt angle, it abuts against first frame 1. On the other hand, as can be seen in FIGS. 3 and 7 to 9, second frame 2 is also equipped with a blocking plate 17a that emerges laterally from second frame 2. Blocking plate 17a is arranged in such a manner that it abuts against first frame 1 when the tilt angle between first frame 1 and second frame 2 reaches the maximum preset tilt. The support for auxiliary elements 17c, whose function is to limit tilting and, as can be seen in FIGS. 5 and 6, emerges from side 1e of the first frame 1 pointing towards side 1b of the same frame, has an analogous function to that of blocking plate 17a; that is, the blocking support 17c abuts against second frame 2 when the maximum preset tilting angle is reached between the first and second frames. Additionally, support 17c may be used to anchor on it auxiliary elements such as electric lines, water conduits, etc. Finally, FIGS. 2 and 3 also show an adjustable tilt blocking system 17b that comprises a pneumatic actuator blocker connected by its lower end to side 1a of the first frame 1 and by its upper part to the neighboring end of second frame 2. The actuator allows the free tilting of first frame 1 in relation to second frame 2, provided it is not activated. When the actuator is activated, regardless of the position of first frame 1 in relation to second frame 2 at the time, prevents the tilting movement, and therefore ensures that the relative position of first frame 1 from second frame 2 is kept constant. When the actuator is returned to inactivity, free tilting can be resumed for the first frame 1 in relation to second frame 2.

I claim:

1. A head for ultrasonic inspections, comprising a semidry coupling system formed by a roller susceptible to roll over a surface of a piece to be inspected and in which is housed at least one ultrasonic head for ultrasonic inspection by pulse echo of carbon fiber pieces, in an automatic inspection facility that comprises a first frame to which the roller is connected and that pivots around a stationary axle arranged perpendicular to the direction of movement of the at least one ultrasonic head; a second frame from which several vertical linear guides emerge and which is connected so as to be able to tilt relative to the first frame; a third frame that slides vertically on the linear guides; coupling means that serve to attach the third frame to the automatic inspection facility; wherein said head further comprises at least, two vertically adjusting actuators selected between pneumatic actuators, electromechanic actuators, and hydraulic actuators anchored each of them by their upper end to the third frame and by the lower end to the second frame;

corresponding laterally aligned pivot axles that are rotatingly connected to the first frame located parallel to and at a lower plane from said stationary axle, and to the respective ends of the stationary axle of the roller through corresponding vertical connection means;

first and second articulation means that connect the first frame to the second frame in such a manner that the first and second frames can tilt mutually around a pivot axle that is perpendicular to the stationary axle.

2. The head according to claim 1 wherein the first frame is a quadrangular frame that comprises two first opposite sides from which the corresponding vertical plates emerge downwardly and to which each of them one of the pivot axles is connected;

two second opposite sides on which the first articulation means are arranged, and which are complementary to the second articulation means that are arranged on the second frame.

3. The head according to claim 2 wherein the first articulation means are corresponding to an articulation axis that from opposite sides of the first frame, and in that the second articulation means are complementary housings located on the corresponding plates that emerge downwardly facing from the opposite sides of the second frame.

4. The head according to claim 1 wherein the first articulation means are corresponding to an articulation axis that from opposite sides of the first frame, and in that the second articulation means are complementary housings located on the corresponding plates that emerge downwardly facing from the opposite sides of the second frame.

5. The head according to claim 1 wherein the third frame comprises a central part bounded between corresponding end parts, and in that the opposite sides of each of the end parts of the third frame corresponding linear bearings are placed to bear respective linear guides that extend over them.

6. The head according to claim 1 wherein each pneumatic actuator is located in an intermediate position between a pair of linear guides.

7. The head according to claim 1 wherein the vertical connection means comprise corresponding vertical clamps each of them comprising an upper part connected to the corresponding end of the stationary axle and a lower part that is rotatably connected to one of the pivot axles; and corresponding housings inside which the pivot axles rotate.

8. The head according to claim 1 wherein the pivot axles are coupled to the first frame by adjusting means to ensure the perpendicularity of the roller.

9. The head according to claim 8 wherein the adjusting means are self-aligning ball bearings.

10. The head according to claim 1 further comprising at least a maximum tilt sensor located in the first frame and connected to an electronic control system.

11. The head according to claim 1 further comprising water atomized spray nozzles placed on the second frame and oriented so as to spray atomized water at least over the roller, and in that the roller has a hydrophilic plastic cladding elastically deformable.

12. The head according to claim 1 further comprising at least a blocking system to block tilting movements between the first and the second frames.

13. The head according to claim 12 wherein the blocking system comprises at least a blocking plate that emerges laterally from the second frame and that is arranged in such a manner as to abut against the first frame when the tilting movement between the first frame and the second frame reaches a preset maximum tilt angle.

14. The head according to claim 13 wherein the blocking system comprises at least an adjustable tilt blocking system that comprises a blocking actuator selected amongst pneumatic actuators, electromechanic actuators and hydraulic actuators and connected by a lower end to one the first sides of the first frame and by an upper end to the second frame.

15. The head according to claim 13 wherein the blocking system comprises at least a support for auxiliary elements that limits tilt and emerges from one of the second sides of the first frame pointing in the direction of one of the first sides of the first frame, in such a manner as to abut against the second frame when the tilting motion between the first frame and the second frame has reached the preset maximum tilt angle.

16. The head according to claim 12 wherein the blocking system comprises at least an adjustable tilt blocking system that comprises a blocking actuator selected amongst pneumatic actuators, electromechanic actuators and hydraulic actuators and connected by a lower end to one the first sides of the first frame and by an upper end to the second frame.

17. The head according to claim 12 wherein the blocking system comprises at least a support for auxiliary elements that limits tilt and emerges from one of the second sides of the first frame pointing in the direction of one of the first sides of the first frame, in such a manner as to abut against the second frame when the tilting motion between the first frame and the second frame has reached the preset maximum tilt angle.

* * * * *